US009808169B2

(12) United States Patent
Similowski et al.

(10) Patent No.: US 9,808,169 B2
(45) Date of Patent: Nov. 7, 2017

(54) SYSTEM FOR ELECTROENCEPHALOGRAPHIC DETECTION OF AN INADEQUACY BETWEEN THE STATE OF A PATIENT PLACED UNDER VENTILATORY SUPPORT AND THE SETTING OF THE MACHINE USED FOR THIS SUPPORT, AND USE OF THIS DETECTION TO ADJUST THE SETTING

(75) Inventors: Thomas Similowski, Issy les Moulineaux (FR); Mathieu Raux, Paris (FR); Louise Tyvaert, Lille (FR)

(73) Assignees: UNIVERSITE PIERRE ET MARIE CURIE (PARIS 6), Paris (FR); ASSISTANCE PUBLIQUE-HOPITAUX DE PARIS, Paris (FR); UNIVERSITE LILLE 2 DROIT ET SANTE, Lillie (FR); CENTRE HOSPITALIER UNIVERSITAIRE DE LILLE, Lillie (FR)

( * ) Notice: Subject to any disclaimer, the term of this patent is extended or adjusted under 35 U.S.C. 154(b) by 1130 days.

(21) Appl. No.: 13/808,424

(22) PCT Filed: Jul. 6, 2011

(86) PCT No.: PCT/FR2011/051611
§ 371 (c)(1),
(2), (4) Date: Apr. 23, 2013

(87) PCT Pub. No.: WO2012/004534
PCT Pub. Date: Jan. 12, 2012

(65) Prior Publication Data
US 2013/0204150 A1    Aug. 8, 2013

(30) Foreign Application Priority Data

Jul. 7, 2010 (FR) ..................... 10 55515

(51) Int. Cl.
*A61B 5/04* (2006.01)
*A61B 5/048* (2006.01)
(Continued)

(52) U.S. Cl.
CPC .......... *A61B 5/04014* (2013.01); *A61B 5/048* (2013.01); *A61B 5/08* (2013.01);
(Continued)

(58) Field of Classification Search
CPC ...... A61M 2230/10; A61B 5/048; A61B 5/08; A61B 5/0476
See application file for complete search history.

(56) References Cited

U.S. PATENT DOCUMENTS 5,520,192 A     5/1996 Kitney et al.
8,032,209 B2 * 10/2011 He ..................... A61B 5/04008
                                                    600/544
(Continued)

FOREIGN PATENT DOCUMENTS

FR    2903314 A1    1/2008
WO    00/00245 A1    1/2000

OTHER PUBLICATIONS

K J Blinowska: "Methods of localization of time-frequency specific activity and estimation of information transfer in brain", International Journal of Bioelectromagnetism, vol. 10, No. 1, 2008, pp. 2-16, XP002627002.
(Continued)

*Primary Examiner* — Jacqueline Cheng
*Assistant Examiner* — Michael Catina
(74) *Attorney, Agent, or Firm* — Troutman Sanders LLP

(57) ABSTRACT

The invention relates to a system for electroencephalographic detection of an improper adjustment of a ventilator used on a mammal. The system includes an electroencephalograph, capable of measuring, as a function of time, an
(Continued)

electroencephalographic signal representative of a breathing process; and an input for receiving a respiratory initiation signal, different from the electroencephalographic signal, capable of indicating a respiratory initiation time. The detection system further includes means for specifying a beta frequency band comprised between 15 and 30 Hz and with a width comprising between 5 and 10 Hz; means for processing the measured electroencephalographic signal, configured for processing the measured electroencephalographic signal as it is being acquired, in the sole specified beta frequency band; and means for identifying, for each breathing cycle, an improper adjustment of the ventilator from the electroencephalographic signals processed in the sole beta frequency band.

10 Claims, 6 Drawing Sheets

(51) Int. Cl.
      *A61B 5/08*      (2006.01)
      *A61M 16/00*    (2006.01)
      *G06K 9/00*      (2006.01)
      *A61B 5/00*      (2006.01)

(52) U.S. Cl.
    CPC .... *A61M 16/0051* (2013.01); *A61M 16/0057* (2013.01); *G06K 9/00536* (2013.01); *A61B 5/726* (2013.01); *A61M 2205/502* (2013.01); *A61M 2230/10* (2013.01)

(56) References Cited

U.S. PATENT DOCUMENTS

2004/0254493 A1* 12/2004 Chervin ................ A61B 5/048
                                                               600/544
2007/0038382 A1    2/2007 Keenan
2009/0241946 A1* 10/2009 Simlowski ........... A61B 5/0476
                                                             128/202.22

OTHER PUBLICATIONS

International Search Report, dated Oct. 4, 2011, which issued during the prosecution of International Patent Application No. PCT/FR2011/051611.

* cited by examiner

SYSTEM FOR ELECTROENCEPHALOGRAPHIC DETECTION OF AN INADEQUACY BETWEEN THE STATE OF A PATIENT PLACED UNDER VENTILATORY SUPPORT AND THE SETTING OF THE MACHINE USED FOR THIS SUPPORT, AND USE OF THIS DETECTION TO ADJUST THE SETTING

CROSS-REFERENCE TO RELATED APPLICATIONS

This application is the National Stage of International Application PCT/FR2011/051611 ("PCT '611") filed Jul. 6, 2011, and published as WO 2012/004534 on Jan. 12, 2012. PCT '611 claims priority to French Application No. 1055515 filed Jul. 7, 2010. All applications noted above are incorporated by reference herein.

FIELD OF INVENTION

The present invention relates to a system for electroencephalographic detection of an improper adjustment of a ventilator used on a mammal, using an electroencephalograph and an input for receiving a respiratory initiation signal.

BACKGROUND

Some persons suffer from acute respiratory failure, for example consecutive to pneumonia, pulmonary edema or superinfection of chronic respiratory diseases. Mechanical ventilatory support may prove to be necessary for these persons. Ventilatory support machines or ventilators include means for detecting inspiration by the patient and means for assisting the patient with inspiration by increasing the flow or pressure of the air collected by the patient. The ventilators also include means for detecting expiration and means for interrupting the inspiratory activity of the ventilator when expiration is detected, which allows synchronizing at best the activity of the patient and that of the ventilator.

Thus, the support consists in providing a predetermined volume of gas or in pressurization of the airways. In both cases, various settings allow the gas flow to be adapted to the needs of the patient. The support machine has to be adapted to the ventilatory behavior of the patients so that the relationship which binds them is "harmonious", i.e. the patient is in a satisfactory physical comfort condition, in which the patient does not feel any difficulty in breathing during ventilatory support. With inadequate adjustments, for example when the provided airflow is too high or, on the contrary, too low, the patient may be in an uncomfortable situation, or even be in a respiratory distress situation. The same applies when the inspiratory activity of the ventilator continues while the patient is in an expiration phase. It seems that such circumstances are deleterious for the patient.

In order to detect such a disharmony between the patient and the ventilator, resulting from improper adjustment of the ventilator, different means have been used. In particular, it is possible to simply question the patient. However, this is not possible when the patient is asleep or in a coma.

It is also possible to observe the ventilatory activity of the patient, and notably the frequency and the use of the different respiratory muscle groups.

Finally, it is possible to study pressure and flow rate signals provided by the ventilator for detecting the occurrence of events showing imperfect synchronization of the ventilator and of the patient. There exist various profiles showing this imperfect synchronization, such as for example "ineffective appeals", during which the patient makes an inspiratory effort which is not "rewarded" by the ventilator.

In practice, these means prove to be delicate to use and are all indirect witnesses of the sensations which the patient may feel.

French Patent Publication No. 2 903 314 ("FR '314") describes a method for detecting a disharmony between a patient and a ventilator consisting, for each breathing cycle, of measuring an electroencephalographic signal over a measurement interval extending around a respiratory initiation time, and of then averaging the electroencephalographic signals measured over several measurement intervals and finally processing the thereby obtained averaged signal in order to infer therefrom possible disharmony between the patient and the ventilator.

Such a method does not give entire satisfaction. Indeed, in situations of discomfort or respiratory distress resulting from disharmony between the patient and the ventilator, it is important to be able to detect this disharmony and to find a remedy thereto as rapidly as possible for restoring harmony between the patient and his/her ventilator.

The method as described in FR '314, requires measurement and averaging of an electroencephalographic signal over at least sixty to eighty breathing cycles so as to be able to conclude that disharmony exists. This on average corresponds to a duration of four to five minutes, during which the detected disharmony is by definition not subject to a correction, whether this correction is carried out by a physician alerted by the identification of the abnormal electroencephalographic signal, or by the activation of a control loop on the ventilator. Moreover, the signal measured by the averaging process, called a pre-motor potential, may easily be subject to interferences, either due to the movements of the patient or due to the electromagnetic pollution characteristic of resuscitation and intensive care environments. Thus, it appears to be desirable to improve both the reactivity and the reliability of electroencephalographic detection of patient-ventilator disharmony.

An object of the invention is therefore to provide a system for electroencephalographic detection of an improper adjustment of a ventilator which is more reliable, and in particular which allows detection in real time of disharmony and therefore of an improper adjustment of a ventilator.

SUMMARY

For this purpose, the object of the invention is a system for detecting an improper adjustment of the aforementioned type, characterized in that the detection system further includes means for specifying a beta frequency band comprised between 15 and 30 Hz and with a width comprised between 5 and 10 Hz; means for processing the measured electroencephalographic signal, configured for processing the measured electroencephalographic signal as it is being acquired, in the sole specified beta frequency band; and means for identifying, for each breathing cycle, an improper adjustment of the ventilator from the electroencephalographic signals processed in the sole beta frequency band.

According to particular examples, the system for detecting an improper adjustment according to the invention includes one or more of the following features, taken individually or according to all technically possible combination(s):

the means for identifying an improper adjustment are configured for identifying for each breathing cycle, possible desynchronization of the electroencephalographic signal in the specified beta frequency band, said desynchronization preceding the respiratory initiation time;

the processing means further includes computation means, configured for calculating the instantaneous power in the sole beta frequency band of the electroencephalographic signal, as well as storage means capable of storing the calculated instantaneous power;

the computation means are able to calculate, for each breathing cycle, from the instantaneous power, an average power of the electroencephalographic signal in the sole beta frequency band over a first interval, the identification means comprise means for comparing the instantaneous power calculated in a second interval extending in advance of the respiratory initiation time, with the average power calculated over the first interval, the first interval extending in advance of the second interval, and the identification means further comprise detection means able to detect, for each breathing cycle, a deviation between the average power calculated in the first interval and the instantaneous power calculated in the second interval;

the identification means has means for triggering an indicator, able to trigger an indicator if a deviation is detected for a predetermined number of successive breathing cycles;

the detection system further includes, at the input of the means for specifying the beta frequency band, means for determining the beta frequency band, said means for determining the beta frequency band including means for establishing a time-frequency map of the electroencephalographic signal measured by the electroencephalograph, said time-frequency map being able to the change in the power spectral density of the electroencephalographic signal as a function of time and of the frequency of said signal and means for detecting a frequency band in which the power spectral density of the electroencephalographic signal varies by a value above a predetermined threshold, this frequency band corresponding to the beta frequency band specified by the specification means; and the means for determining the beta frequency band further include means for back-averaging point by point the electroencephalographic signal over several identical time intervals, set each on successive respiratory initiation times, each interval partly extending in advance of the respiratory initiation time, and the time-frequency map is obtained from the averaged electroencephalographic signal.

The object of the invention is also a ventilatory support installation characterized in that it includes a ventilator and a system for electroencephalographic detection of an improper adjustment as described earlier.

According to particular embodiments, the ventilatory support installation further has a feedback control loop, capable of modifying the adjustment of the ventilator according to measurements carried out by the system for electroencephalographic detection of an improper adjustment.

The object of the invention is also a method for detecting an improper adjustment of a ventilator used on a mammal, characterized in that it includes the steps of receiving a measurement of an electroencephalographic signal as a function of time; determining, for each breathing cycle, a respiratory initiation time; specifying a beta frequency band comprised between 15 and 30 Hz and with a width comprised between 5 and 10 Hz; processing the measured electroencephalographic signal gradually during its acquisition, in the sole beta frequency band; and identifying, for each breathing cycle, an improper adjustment of the ventilator from the electroencephalographic signal processed in the sole beta frequency band.

The object of the invention is also a computer program product including instructions which, when they are applied on a computer associated with an electroencephalographic, carries out the method as described earlier.

BRIEF DESCRIPTION OF THE DRAWINGS

The invention will be better understood upon reading the description which follows, only given as an example and made with reference to the appended drawings, wherein.

DETAILED DESCRIPTION

Figure 1:
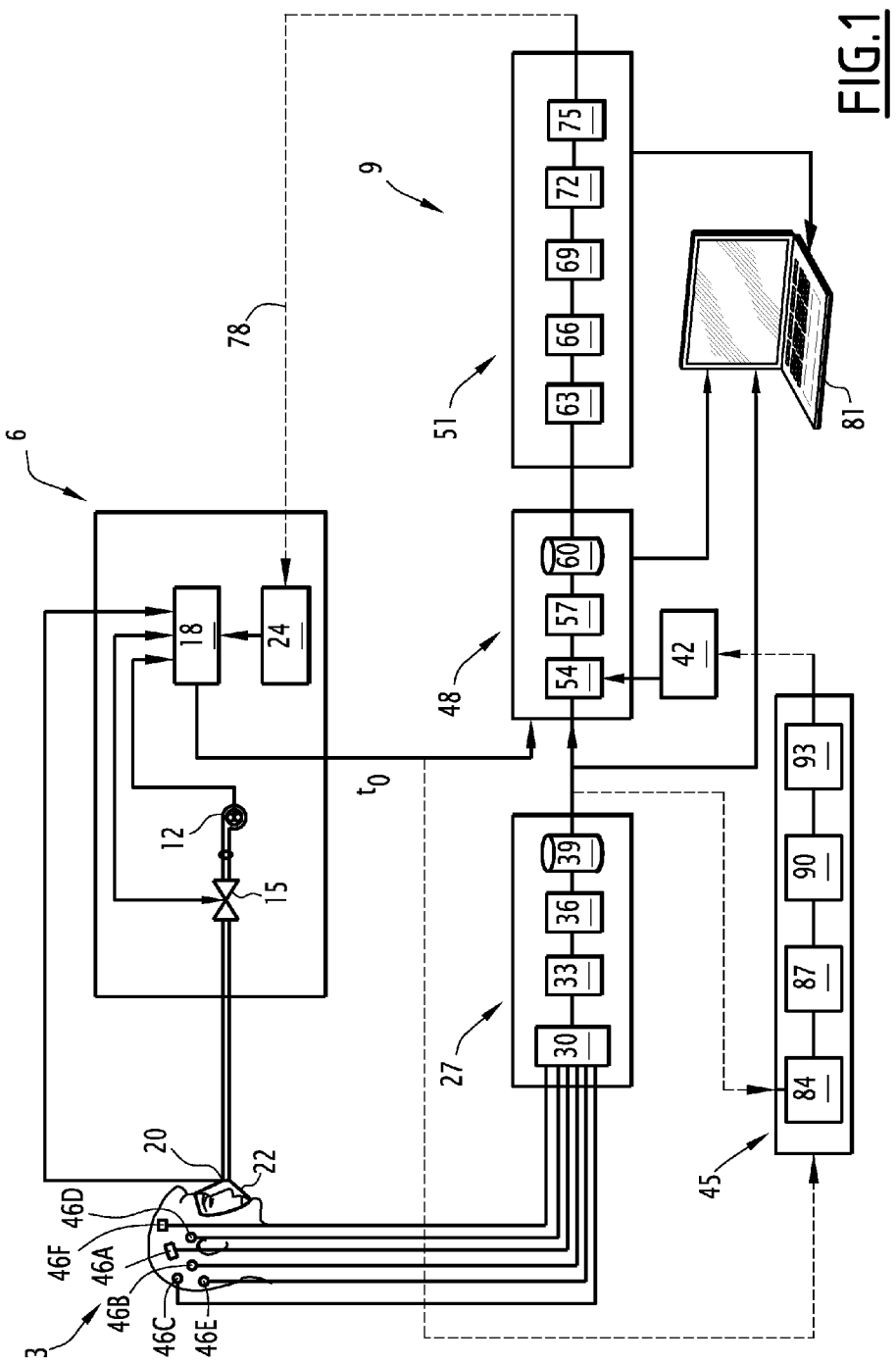
FIG. 1 is a schematic view of a ventilatory support installation applied on a patient.

FIG. 1 illustrates a ventilatory support installation 3 using a system for electroencephalographic detection of an improper adjustment according to examples of the invention.

This installation 3 includes a mechanical ventilator 6 and a system 9 for detecting an improper adjustment of the ventilator 6.

The ventilator 6 includes a turbine 12 able to provide an airflow to a patient at a determined flow rate and with a given pressure. At the outlet of the turbine 12 a valve 15 is provided for feeding or not feeding the pressurized air produced by the turbine 12 to the patient. The turbine 12 and the valve 15 are connected to a control unit 18, itself connected to a depression sensor 20 able to detect inspiration of the patient.

The turbine 12 is connected, downstream from the valve 15, to a mask 22 which may be applied onto the upper airways of the patient. The depression sensor 20 is for example mounted in the mask 22 of the patient.

Alternatively, the mask 22 may be replaced with an endotracheal probe.

The control unit 18 is connected to an adjustment unit 24 capable of modifying the operating parameters of the machine 6, and in particular the flow rate imposed by the turbine 12, the pressure of the air flow, the switching instants of the valve 15, and any other parameter as known in the state of the art. Moreover, the control unit 18 includes an output capable of providing a respiratory initiation signal $t_0$ representative of the start of an inspiration of the patient. In this embodiment, the respiratory initiation time $t_0$ is detected by the control unit 18 by means of the depression sensor 20. According to an alternative, the respiratory initiation time $t_0$ corresponds to a signal emitted by the machine 6 when it begins to provide air to the patient.

In the following, by breathing cycle is meant the time interval corresponding to an expiration followed by a complete inspiration. Each breathing cycle extends around a respiratory initiation time $t_0$.

The system 9 for detecting an improper adjustment includes an electroencephalograph 27, capable of measuring an electroencephalographic (EEG) signal representative of breathing, and capable of providing an EEG signal s(t) as a function of time. Such a signal s(t) is illustrated by curve 1 of FIG. 2.

The electroencephalograph 27 for example includes between 2 and 64 electrodes positioned on the skull of the patient and notably at the supplementary motor area, i.e. the premotor cortex. In the illustrated embodiment, the electroencephalograph 27 includes 6 electrodes 46A, 46B, 46C, 46D, 46E, 46F. In this embodiment, the electrodes 46E and 46F are a reference electrode and a ground electrode respectively. The use of six electrodes 46A, 46B, 46C, 46D, 46E, 46F is a typical configuration for use in resuscitation. The electrodes 46A, 46B, 46C, 46D, 46E, 46F may be of any nature; they are notably needle electrodes or surface electrodes.

As known, the electroencephalograph 27 includes means 30 for collecting the electroencephalographic signal s(t), filtering and amplification means 33, capable of filtering the measured electroencephalographic signal s(t), for example in a frequency band comprised between 0.03 and 40 Hz as well as sampling means 36 in order to digitize the EEG signal s(t), for example with a sampling frequency of 256 Hz. It further includes computer means 39 for storing the sample values, associated with their respective sampling instants.

The system 9 also includes means 42 for specifying a beta frequency band, comprised between 15 and 30 Hz and with a width comprised between 5 and 10 Hz. This beta frequency band corresponds to the frequency band of the EEG, in which, during motor execution of a cortical command, a reduction in the power of the EEG signal is observed before the instant at which execution of the movement starts, followed by an increase in the power of the EEG signal, after the instant at which execution of the movement starts. This reduction in the power corresponds to the phenomenon of event-related desynchronization, while the increase in the power corresponds to the phenomenon of movement-related synchronization. The beta frequency band varies depending on the patient.

The specification means 42 for example comprise a computer input interface, configured for receiving lower limit and upper limit values of the beta frequency band, inputted by a user.

Alternatively, the specification means 42 are connected to the output of means 45 for determining the beta frequency band, as described later on.

The system 9 further includes a unit 48 for processing the measured electroencephalographic signal s(t), which has an input connected to the electroencephalograph 27 for receiving the electroencephalographic signal s(t) provided by the electroencephalograph 27. The processing unit 48 includes an input for receiving the respiratory initiation signal $t_0$, connected to the corresponding output of the machine 6, as well as an input for receiving the beta frequency band, connected to the output of the specification means 42.

At its output, the processing unit 48 is connected to means 51 for identifying an improper adjustment of the ventilator 6.

The processing unit 48 is able to process the electroencephalographic signal s(t) provided by the electroencephalograph 27 in the sole beta frequency band specified via specification means 42 as this signal s(t) is being acquired by the electroencephalograph 27.

The processing unit 48 comprises filtering means 54, able to filter the EEG signal s(t) provided by the electroencephalograph 27, in the beta frequency band specified by the specification means 42, so as to only keep the components of the EEG signal s(t) with a frequency comprised in the beta frequency band. The filtering means 54 for example comprise a filter with an infinite pulse response of the order of 6. The filtering means 54 are capable of providing at the output an EEG signal s'(t) in the sole beta frequency band, an example of which is illustrated by curve 2 of FIG. 2.

Figure 2:
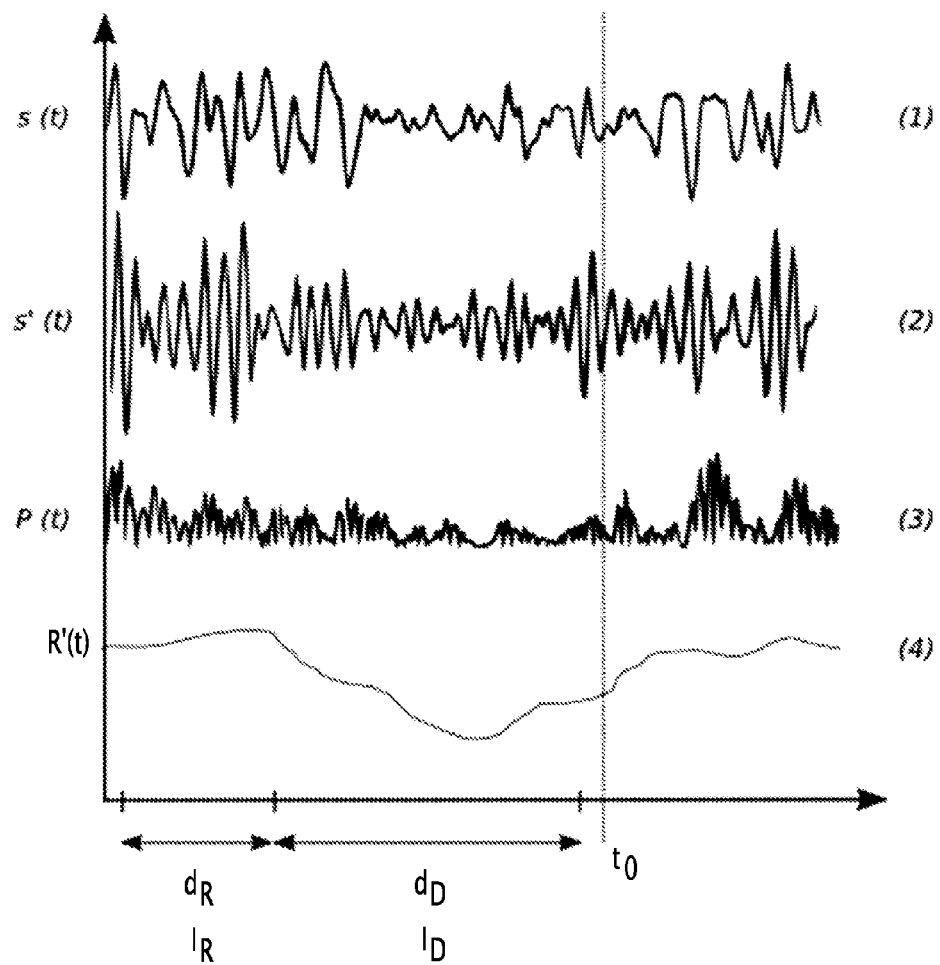
FIG. 2 is an example of curves illustrating steps for processing an electroencephalographic signal by the system for electroencephalographic detection on an improper setting according to an example of the invention.

The filtering means 54 are connected at the output to computation means 57, capable of calculating the instantaneous power P(t) of the EEG signal s'(t) in the sole beta frequency band. For this purpose, the computation means 57 are capable of calculating the square of the modulus of the amplitude of the electroencephalographic signal s'(t) by applying the following formula: $P(t)=|s'(t)|^2$. The curve 3 of FIG. 2 illustrates an example of the thereby calculated instantaneous power P(t).

According to an example, the computation means 57 are further configured for computing, for each respiratory cycle comprising a respiratory initiation time $t_0$, the average power $P_{mD}$ of the EEG signal s'(t) in the sole beta frequency band, over an interval $I_D$, of duration $d_D$, extending in advance of the respiratory initiation time $t_0$, as well as the average power $P_{mR}$ of this signal s'(t) over an interval $I_R$, of duration $d_R$, extending in advance of the interval $I_D$.

The beginning of the interval $I_D$ precedes the respiratory initiation time $t_0$ by less than 2 seconds. The beginning of the interval $I_R$ precedes the respiratory initiation time $t_0$ by 3.5 to 1 second.

The duration $d_D$ of the interval $I_D$ is comprised between 0.125 and 2 seconds. The interval $I_D$ entirely extends before the respiratory initiation time $t_0$. The duration $d_R$ of the interval $I_R$ is comprised between 0.1 and 0.5 seconds. The interval $I_R$ extends in advance of the interval $I_D$ and does not overlap the interval $I_D$.

In order to calculate the average power $P_{mD}$ of the signal s'(t) over the interval $I_D$, the computation means 57 are for example configured for applying the following formula (1):

$$P_{mD} = \frac{1}{t_2 - t_1} \int_{t=t1}^{t=t2} P(t)\,dt \qquad (1)$$

wherein $t_1$ corresponds to the instant of the beginning of the interval $I_D$;

$t_2 = t_1 + d_D$; and

P(t) is the instantaneous power of the EEG signal s'(t) in the sole beta frequency band, calculated by the computation means 57.

In order to calculate the average power $P_{mR}$ of the signal s'(t) over the interval $I_R$, the computation means 57 are configured for applying the formula (1), $t_1$ corresponding to the instant of the beginning of the interval $I_R$ and $t_2=t_1+d_R$.

The processing unit 48 further comprises storage means 60 capable of storing the instantaneous power P(t), as well as the average powers $P_{mD}$ and $P_{mR}$ calculated by the computation means 57.

The means 51 for identifying an improper adjustment of the machine 6 are capable of identifying, for each breathing cycle, possible desynchronization of the EEG signal s'(t) in the specified beta frequency band.

The identification means 51 includes comparison means 63, configured for comparing, for each breathing cycle, the average power $P_{mD}$ calculated over the interval $I_D$ with the average power $P_{mR}$, calculated over the interval $I_R$. For this purpose, they are for example configured for calculating, for each breathing cycle, an average desynchronization ratio R, representative of a desynchronization of the EEG signal s'(t) in the beta frequency band, by applying the following formula:

$$R = \frac{P_{mD} - P_{mR}}{P_{mR}} \times 100$$

wherein $P_{mD}$ is the average power of the signal s'(t) over the interval $I_D$; and $P_{mR}$ is the average power of the signal s'(t) over the interval $I_R$.

The identification means 51 further has detection means 66 capable of detecting, for each breathing cycle, whether there exists desynchronization of the EEG signal s'(t). The detection means 66 are capable of comparing, for each breathing cycle, the average desynchronization ratio R, with a predetermined value noted as V. The predetermined value V is for example equal to −15%. If the detection means 66 detect an average desynchronization ratio R less than the predetermined value V, a counter 69 of the detection system 9 is incremented.

If the detection means 66 detect that the average desynchronization ratio R is not less than the predetermined value V, the counter 69 is reset to zero.

According to another example, the computation means 57 of the processing unit 48 are capable of calculating the average power $P_{mR}$ over the interval $I_R$ in the way described above, and the comparison means 63 of the identification means 51 are configured for calculating over the interval $I_D$, an instantaneous desynchronization ratio R'(t) by applying the following formula:

$$R'(t) = \frac{P(t) - P_{mR}}{P_{mR}} \times 100$$

wherein:

P(t) is the instantaneous power of the signal s'(t) over the interval $I_D$; and $P_{mR}$ is the average power of the signal s'(t) over the interval $I_R$.

Figure 3:
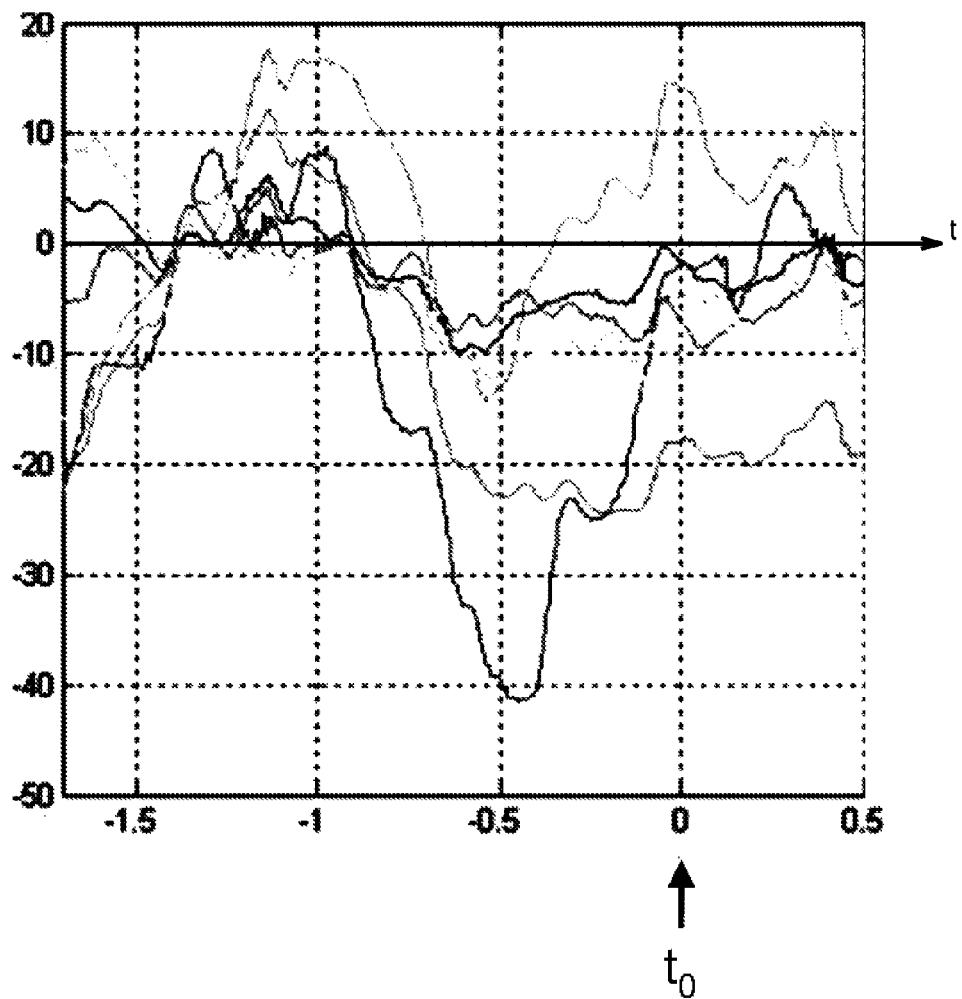
FIG. 3 is an example of a set of curves, obtained from electrodes placed in different localizations, and illustrating, as a function of time, the change in a desynchronization ratio of an electroencephalographic signal collected for a patient placed under ventilatory support, in the presence of disharmony between the patient and the ventilator.
Figure 4:
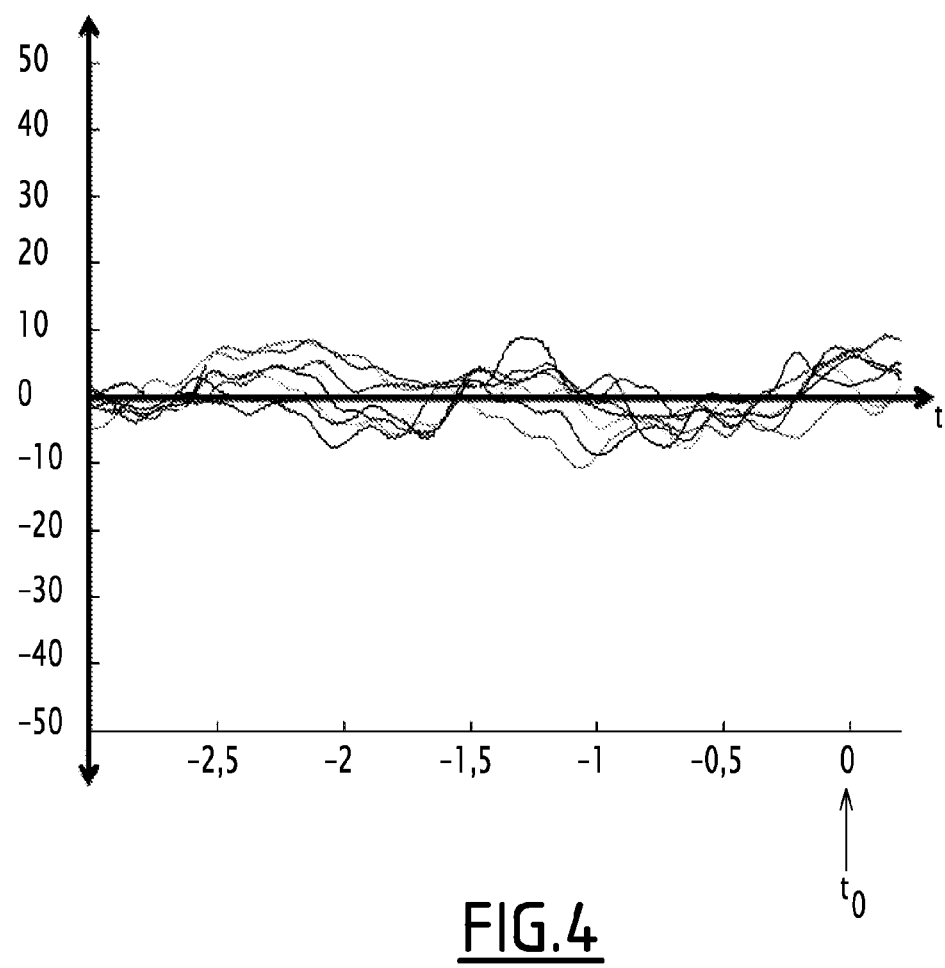
FIG. 4 is a view similar to that of FIG. 3, in the absence of disharmony between the patient and the ventilator.

The curve 4 of FIG. 2 illustrates change in the instantaneous desynchronization ratio R'(t) of the signal s'(t) as a function of time. The sets of curves of FIGS. 3 and 4 illustrate the change in the instantaneous desynchronization ratio R'(t) of the signal s'(t), in the presence of desynchronization and in the absence of desynchronization, respectively. The curves of FIGS. 3 and 4 are respectively obtained by applying the processing steps indicated above to the signal s(t) stemming from electrodes placed at different bypasses. FIGS. 3 and 4 were obtained with a different number of electrodes.

According to this example, the detection means 66 are configured for applying, for the whole of the values of the instantaneous desynchronization ratio R'(t) a statistical test, for example a Wilcoxon test, in order to determine, for each breathing cycle, whether there exists a deviation expressing desynchronization between the power P(t) of the signal s'(t) in the interval $I_D$ and the average power $P_{mR}$ of the signal s'(t) in the interval $I_R$. In the case when the detection means 66 are configured for applying a Wilcoxon test, the null hypothesis is rejected if the first species risk is less than 1%, i.e. a deviation expressing desynchronization is seen if the first species risk is less than 1%.

According to a further example, the computation means 57 of the processing unit 48 are configured for calculating the average power $P_{mR}$ over the interval $I_R$ in the way described above, and the detection means 66 are configured for applying, for the whole of the values of the instantaneous power P(t) calculated over the interval $I_D$, a statistical test, for example a Wilcoxon test, in order to determine, for each breathing cycle, whether there exists a deviation expressing desynchronization between the power P(t) of the signal s'(t) in the interval $I_D$ and the average power $P_{mR}$ of the signal s'(t) in the interval $I_R$. In the case when the detection means 66 are configured for applying a Wilcoxon test, the null hypothesis is rejected if the first species risk is less than 1%, i.e. a deviation expressing desynchronization is seen if the first species risk is less than 1%.

According to these examples, at each breathing cycle, if the detection means 66 detect a deviation expressing desynchronization between the power P(t) of the signal s'(t) in the interval $I_D$ and the average power $P_{mR}$ of the signal s'(t) in the interval $I_R$, the counter 69 is incremented.

If the detection means 66 do not detect any deviation expressing desynchronization between the power P(t) of the signal s'(t) in the interval $I_D$ and the average power $P_{mR}$ of the signal s'(t) in the interval $I_R$, the counter 69 is reset to zero.

An EEG signal s(t) may be obtained at the output of the electroencephalograph 27 for each of the electrodes of the electroencephalograph 27. Only one of these signals s(t) has been illustrated in FIG. 2. The detection system 9 according to the invention is capable of applying the same processing operation to the EEG signals s(t) stemming from each of the electrodes of the electroencephalograph 27, so as to obtain an average desynchronization ratio R or an instantaneous desynchronization ratio R'(t) for each of them.

According to an example, only one of the EEG signals s(t) from a particular electrode is taken into account for incrementing or resetting the counter 69 by the detection means 66.

According to an alternative example, the average desynchronization ratio R or instantaneous desynchronization ratio R' obtained from EEG signals s(t) from several electrodes are taken into account for incrementing or resetting the counter 69 by the detection means 66.

The identification means 51 further includes means 72 for triggering an indicator, capable of triggering an indicator 75 when the counter 69 exceeds a predetermined threshold value, i.e. when desynchronization has been detected for a predetermined number of successive breathing cycles.

The indicator 75 is thus able to indicate the existence of disharmony between the patients and the support machine 6 to the practitioner. The indicator 75 is for example an indicator light, an acoustic signal or any other suitable means for alarming the practitioner.

According to another example, the trigger means 72 are able to trigger the indicator 75 as soon as the counter 69 becomes greater than 1, i.e. at each breathing cycle for which the detection means 66 detect desynchronization.

According to a further example, a feedback control loop 78 connects the system for detecting an improper adjustment 9 to the support machine 6. The feedback control loop 78 is able to modify the settings of the ventilator 6 when the detection system 9 detects disharmony, i.e. in particular when the indicator 75 is triggered. For this purpose, the feedback control loop 78 is able to apply an algorithm of a known type, capable of modifying the settings of the machine 6 by successive iterations, and capable of being only applied when the system 9 detects disharmony.

The system 9 further includes means 81 for providing a piece of information representative of an improper adjustment of the machine 6 to a practitioner. These information providing means 81 are connected to the identification means 51. For example they comprise a display screen and are capable of displaying for example the curves illustrated in FIG. 2, in particular change of the instantaneous desynchronization ratio R'(t) as a function of time and the EEG signal s(t) recorded by the electroencephalograph 27, as well as the number of breathing cycles associated with desynchronization during the last 20 breathing cycles and the time having elapsed without any desynchronization. In this case, the information providing means 81 are also able to receive information from the electroencephalograph 27 and the processing unit 48.

Optionally, the system 9 for detecting an improper adjustment further comprises means 45 for determining the beta frequency band. These determination means 45 include an input for receiving the EEG signal s(t) provided by the electroencephalograph 27 and an input for receiving the respiratory initiation signal $t_0$, connected to the corresponding output of the support machine 6.

The means 45 for determining the beta frequency band comprise means 84 for segmenting the EEG signal s(t) into identical successive time intervals $I_1, I_2, \ldots, I_n$. Each time interval $I_1, I_2, \ldots, I_n$ comprises a respiratory initiation time $t_0$. Each time interval $I_1, I_2, \ldots, I_n$ has a duration d. The duration d consists of a duration $d_1$ extending in advance with respect to the respiratory initiation time $t_0$ and of a duration $d_2$ extending with delay with respect to the respiratory initiation time $t_0$. The durations d, $d_1$ and $d_2$ are identical for all the intervals $I_1, I_2, \ldots, I_n$.

The duration d is between 0.375 and 3 seconds, the duration $d_1$ between 0.125 and 2 seconds and the duration $d_2$ is between 0.250 and 1 second.

Figure 5:
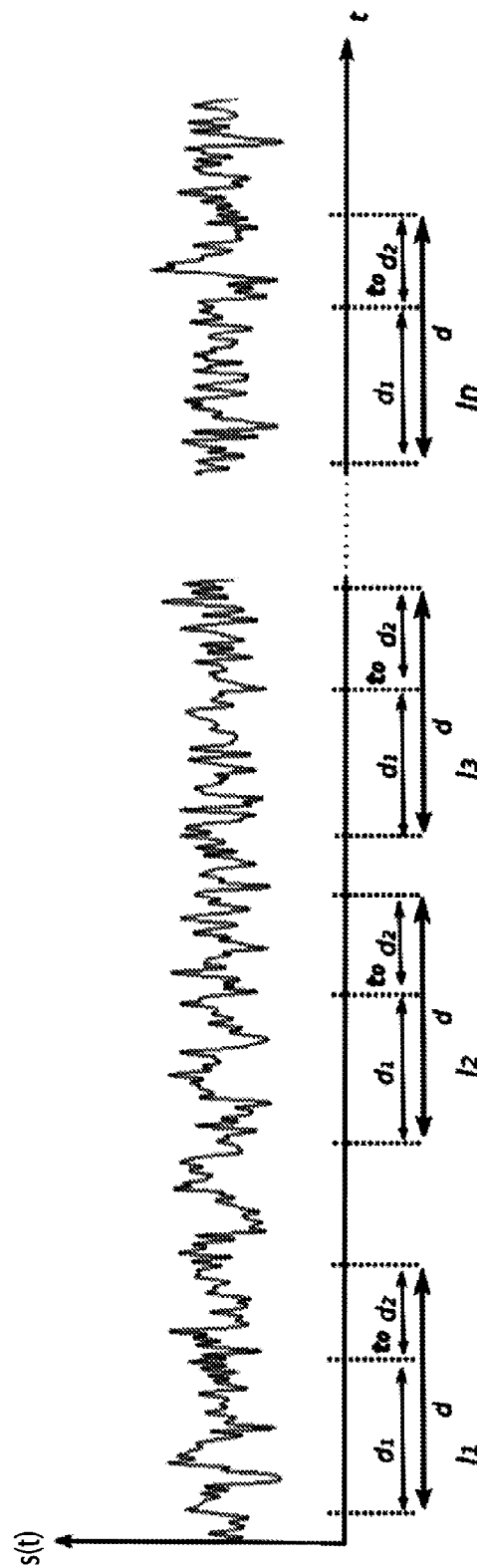
FIG. 5 is an exemplary curve illustrating the change, as a function of time, of an electroencephalographic signal representative of a breathing phenomenon.

FIG. 5 is a schematic illustration of an EEG signal s(t) segmented into intervals $I_1, I_2, \ldots, I_n$ by the segmentation means 84. In this figure, the duration d is equal to 1.5 seconds, the duration $d_1$ to 1,250 milliseconds and the duration $d_2$ to 250 milliseconds.

The means 45 for determining the beta frequency band further comprise means 87 for back-averaging the sampled values of the EEG signal s(t) stored in memory over n successive time intervals $I_1, I_2, \ldots, I_n$, i.e. including successive respiratory initiation times $t_0$. The back-averaging means 87 are for example formed with a microcomputer applying a suitable program. More specifically, the back-averaging means 87 are able to produce the arithmetic mean point by point between the corresponding sampled values of the n successive time intervals $I_1, I_2, \ldots, I_n$ of the recorded EEG signal. The number n of time intervals $I_1, I_2, \ldots, I_n$ is comprised between 20 and 80, and is for example equal to about 30.

Thus, the back-averaging means 87 are configured for providing, from n portions of the signal s(t) over the intervals $I_1, I_2, \ldots, I_n$, an averaged signal $s_m(t)$ over a time interval $I_m$ having the same characteristics as the intervals $I_1, I_2, \ldots, I_n$ and therefore comprising a respiratory initiation time $t_0$.

The means 45 for determining the beta frequency band further comprise means 90 for establishing a time-frequency map, further called a spectrogram, of the averaged signal $s_m(t)$ obtained at the output of the back-averaging means 87. The time-frequency map is able to indicate the change in the power spectral density of the averaged signal $s_m(t)$ as a function of the frequency of said signal $s_m(t)$ and of time.

The means 90 for establishing the time-frequency map are for example configured for applying to the averaged signal $s_m(t)$ a short term Fourier transform or a discrete wavelet transform in order to obtain a transformed signal F(f,t), and then for calculating the power spectral density P(f,t) of the transformed signal F(f,t), this power spectral density P(f,t) corresponding to the square of the modulus of the transformed signal F(f,t). The means 90 for establishing the time-frequency map are further configured in order to represent the power spectral density P(f,t) of the transformed signal F(f,t) as a function of frequency and time on a time-frequency map.

Figure 6:
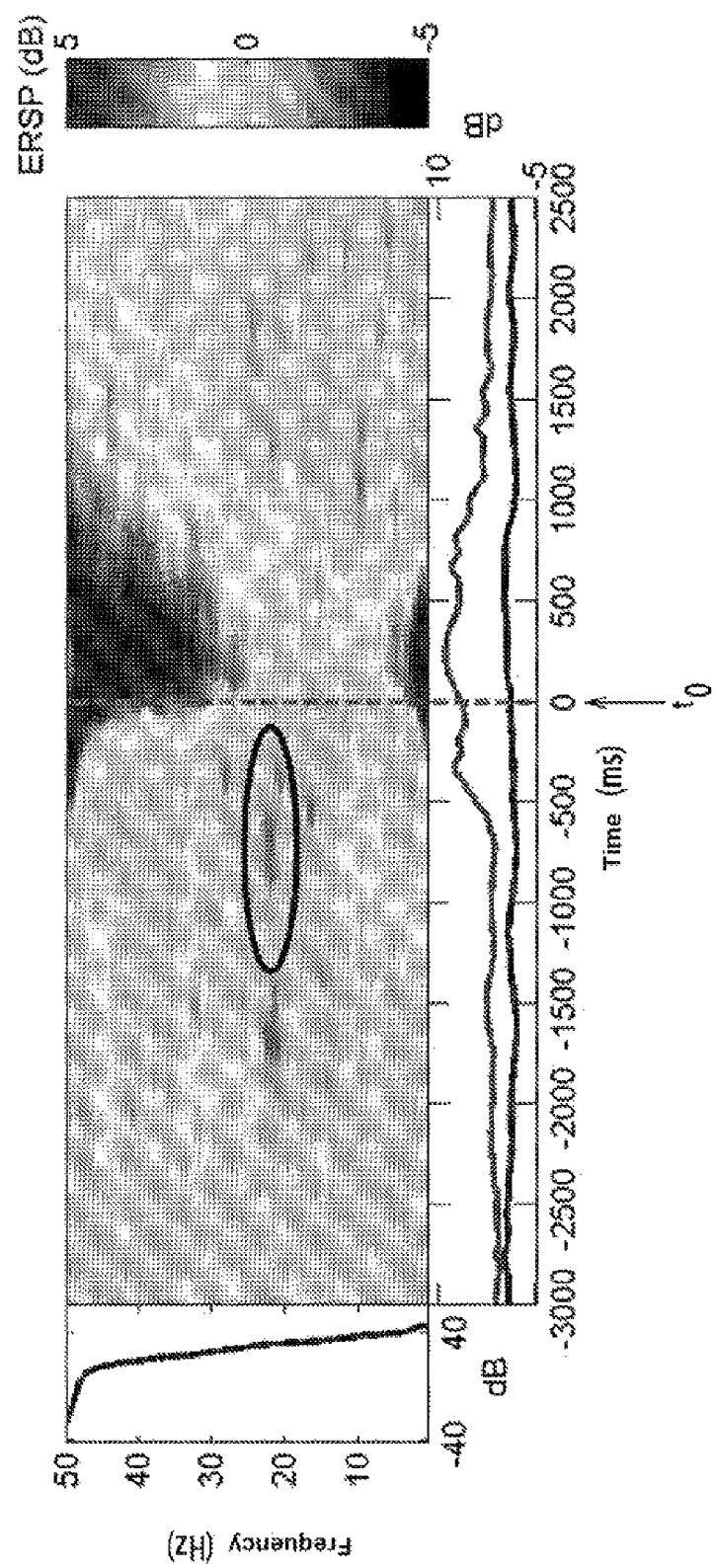
FIG. 6 is an illustration of the electroencephalographic signal of FIG. 5 in the form of a time-frequency map.

According to an example, illustrated in FIG. 6, the power spectral density P(f,t) is expressed in decibels, relatively to a reference power spectral density $P_{ref}$. This quantity is noted as ERSP (Event Related Spectral Perturbation). The reference power spectral density $P_{ref}$ corresponds to the value of the power spectral density P(f,t) of the transformed signal F(f,t) over a reference interval extending in advance with respect to the respiratory initiation time $t_0$. The reference interval has a duration comprised between 150 and 300 ms. The beginning of the reference interval precedes the respiratory initiation time by a duration comprised between 0.1 and 0.5 seconds and for example of about 250 milliseconds. The reference interval further extends in advance with respect to a movement preparation interval, i.e. for preparing the inspiration, and does not overlap this preparation interval. The beginning of the preparation interval precedes the respiratory initiation time $t_0$ by a duration comprised between 0.1 and 0.5 seconds.

Finally, the determination means 45 includes means 93 for detecting the beta frequency band from the time-frequency map established by the means 90 for establishing the time-frequency map.

The means 93 for detecting the beta frequency band are capable of determining the frequency band of the EEG signal s(t) in which there exists, for a predetermined duration, a deviation between the power spectral density P(f,t) of the transformed signal F(f,t) and the reference power spectral density $P_{ref}$, which is greater than a predetermined value. Thus, the detection means 93 are capable of determining the frequency band in which the power spectral density P(f,t) of the transformed signal F(f,t) is less than the reference power spectral density $P_{ref}$ by a value greater than a predetermined value. This predetermined value is for example equal to about 15% and the predetermined duration is for example equal to 100 ms.

In the example illustrated in FIG. 6, the detection means 93 are capable of determining this deviation from the ERSP. They are then capable of determining the frequency band in which, for a predetermined duration, the value of the ERSP is less than −0.7, which corresponds to a variation of 15% between the power spectral density P(f,t) and the reference power spectral density $P_{ref}$, the power spectral density P(f,t) being less by at least 15% than the reference spectral density $P_{ref}$. The thereby determined frequency band corresponds to the beta frequency band. It is materialized by an ellipse in FIG. 6.

As was indicated above, the beta frequency band corresponds to a frequency band of the electroencephalographic signal, in which desynchronization is observable before the beginning of the movement, materialized by the respiratory initiation time $t_0$. Such a desynchronization only occurs in the case of the execution of a cortical command. When the patient is in harmony with the machine 6, there is no cortical motor activity related to breathing. No desynchronization is then observed. The determination of the beta frequency band by the determination means 45 therefore requires that the patient performs, during the number n of successive breathing cycles, voluntary respiratory movements or respiratory movements which are known to respond to a cortical command.

Within the scope of the method for determining the beta frequency band applied by the means 45 for determining the beta frequency band, a first method for generating such voluntary respiratory movements or for are known to respond to a cortical command, consists of voluntarily upsetting the settings of the support machine 6 for a number n of breathing cycles, notably if the patient is in a coma. This upset for example consists in a transient decrease in the sensitivity of the threshold for triggering the support provided by the ventilator 6. Alternatively, if the patient is conscious and able to breathe by himself/herself, he/she performs a number n of voluntary inspirations, for example in the form of maximum voluntary sniffs.

According to an embodiment of the method for detecting an improper adjustment of a ventilator according to the invention, the beta frequency band is determined only once by the means 45 for determining the beta frequency band. According to an alternative, the means 45 for determining the beta frequency band determine the beta frequency band at regular intervals while the patient is artificially ventilated.

The system for detecting an improper adjustment of a ventilator according to the invention has the advantage of not requiring any averaging of the electroencephalographic signal for determining disharmony. Indeed, the system is able to detect the existence of desynchronization, and therefore a voluntary breathing effort, or more generally a breathing effort in response to a cortical command from the patient, which is the sign of a disharmony between the patient and the machine, at each breathing cycle.

Thus, the system according to the invention is able to detect disharmony in real time and to also find a remedy thereto rapidly, by modifying the settings of the ventilator, either automatically via a feedback control loop or manually by a practitioner.

Further, the system according to the invention is able to analyze the signal in a particularly reliable way. Indeed, the filtering of the electroencephalographic signal in the beta frequency band suppresses a certain number of artifacts of the electroencephalographic signal, sources of errors, and notably artifacts related to the movement of the patient, to the cables for collecting the electroencephalographic signal, to the presence of a large number of electrical apparatuses (operating with a frequency of 50 Hz in France and of 60 Hz in the United States) or of artifacts related to the sweating phenomenon of the patient, responsible for variations of the signal in low frequencies, i.e. in frequencies below 1 Hz.

Finally, the desynchronization signal, i.e. the signal representing the instantaneous desynchronization ratio (curve 4 of FIG. 2) has a high signal-to-noise ratio, and notably higher than when a signal, obtained by averaging without any preliminary filtering in the beta band, is used.

The invention claimed is:

1. A system for electroencephalographic detection of an improper adjustment of a ventilator used on a mammal, comprising:
   an electroencephalograph, capable of measuring, as a function of time, an electroencephalographic signal representative of a breathing process;
   an input receiving a respiratory initiation signal, different from the electroencephalographic signal, capable of indicating a respiratory initiation time;
   wherein the detection system further comprises:
   a beta band device specifying a sole beta frequency band comprised between 15 and 30 Hz and with a width comprised between 5 and 10 Hz;
   a processor configured to:
      process the measured electroencephalographic signal as it is being acquired, in the sole specified beta frequency band,
      calculate the instantaneous power of the electroencephalographic signal in the sole beta frequency band, and
      calculate, for each breathing cycle, from the instantaneous power, an average power of the electroencephalographic signal in the sole beta frequency band over a first interval;
   memory, storing the calculated instantaneous power; and
   an identifier identifying, for each breathing cycle, an improper adjustment of the ventilator from the electroencephalographic signals processed in the sole beta frequency band:
      wherein the identifier comprises a comparator comparing the instantaneous power calculated in a second interval extending in advance of the respiratory initiation time with the average power calculated over the first interval, the first interval extending in advance of the second interval, and
      wherein the identifier further comprises a detector, capable of detecting, for each breathing cycle, a deviation between the average power calculated in the first interval and the instantaneous power calculated in the second interval, and
      wherein said deviation comprises a decrease of the instantaneous power calculated in the second interval compared to the average power calculated over the first interval and is representative of an improper adjustment of the ventilator.

2. The electroencephalographic detection system according to claim 1, wherein the identifier identifying the improper adjustment is configured to identify, for each breathing cycle, a possible desynchronization of the electroencephalographic signal in the specified beta frequency band, said desynchronization preceding the respiratory initiation time.

3. The electroencephalographic detection system according to claim 1, wherein the identifier further comprises a trigger capable of triggering an indicator if a deviation is detected for a predetermined number of successive breathing cycles.

4. The electroencephalographic detection system according to claim 1, further comprising, at an input of the beta band device, a beta band determiner determining the beta frequency band, wherein said beta band determiner is also configured to establish a time-frequency map of the electroencephalographic signal measured by the electroencephalograph, wherein said time-frequency map is capable of indicating the change in the power spectral density of the electroencephalographic signal as a function of time and of the frequency of said signal, and a frequency detector detecting a frequency band in which the power spectral density of the electroencephalographic signal varies by a value greater than a predetermined threshold, this frequency band corresponding to the sole beta frequency band specified by the beta band device.

5. The electroencephalographic detection system according to claim 4, wherein the beta band device further comprising a back-averaging device back-averaging point by point the electroencephalographic signal over several identical time intervals, being each set on successive respiratory initiation times, each interval partly extending in advance of the respiratory initiation time, and in that the time-frequency map is obtained from the averaged electroencephalographic signal.

6. A ventilatory support installation, comprising:
a ventilatory support machine, and
a system configured for electroencephalographic detection of an improper adjustment according to claim 1.

7. The ventilatory support installation according to claim 6, further comprising a feedback control loop capable of modifying the adjustment of the ventilator according to the measurements carried out by the system for electroencephalographic detection of an improper adjustment.

8. A method for detecting, via a system for electroencephalographic detection of an improper adjustment of a ventilator, an improper adjustment of a ventilator used on a mammal, comprising the steps:

receiving, from an electroencephalograph, a measurement of an electroencephalographic signal as a function of time;

determining, via an input receiving a respiratory initiation signal, for each breathing cycle, a respiratory initiation time;

specifying, using a beta band device, a beta frequency band comprised between 15 and 30 Hz and with a width comprised between 5 and 10 Hz;

processing, with a processor, the measured electroencephalographic signal, as it is being acquired, in the sole beta frequency band;

calculating, via the processor, the instantaneous power of the electroencephalographic signal in the sole beta frequency band;

calculating, via the processor, for each breathing cycle, from the instantaneous power, an average power of the electroencephalographic signal in the sole beta frequency band over a first interval;

storing, in memory, the calculated instantaneous power; and identifying, via the processor, for each breathing cycle, an improper adjustment of the ventilator based on the electroencephalographic signal processed in the sole beta frequency band;

wherein indentifying an improper adjustment of the ventilator based on the electroencephalographic signal processed in the sole beta frequency band comprises:

comparing the instantaneous power calculated in a second interval extending in advance of the respiratory initiation time with the average power calculated over the first interval, the first interval extending in advance of the second interval, and detecting, for each breathing cycle, a deviation between the average power calculated in the first interval and the instantaneous power calculated in the second interval, wherein said deviation comprises a decrease of the instantaneous power calculated in the second interval compared to the average power calculated over the first interval and is representative of an improper adjustment of the ventilator, and wherein the system for electroencephalographic detection of an improper adjustment of a ventilator comprises the electroencephalograph, an input receiving a respiratory initiation signal, the beta band device, the memory, and the processor.

9. Non-transient memory comprising instructions which, when executed by a system comprising an electroencephalograph, an input receiving a respiratory initiation signal, a beta band device, and a processor, causes the system to carry out the method according to claim 8.

10. The electroencephalographic detection system according to claim 1, wherein the detector is configured for detecting the deviation by applying a statistical test.

* * * * *